US010983104B2

(12) United States Patent
Rodriguez et al.

(10) Patent No.: US 10,983,104 B2
(45) Date of Patent: *Apr. 20, 2021

(54) MICROFLUIDIC CHAMBER ASSEMBLY FOR MASTITIS ASSAY

(71) Applicant: Advanced Animal Diagnostics, Inc., Durham, NC (US)

(72) Inventors: Rodolfo R. Rodriguez, Cary, NC (US); Charles F. Galanaugh, West Milford, NJ (US)

(73) Assignee: Advanced Animal Diagnostics, Inc., Morrisville, NC (US)

( * ) Notice: Subject to any disclaimer, the term of this patent is extended or adjusted under 35 U.S.C. 154(b) by 191 days.

This patent is subject to a terminal disclaimer.

(21) Appl. No.: 14/105,662

(22) Filed: Dec. 13, 2013

(65) Prior Publication Data

US 2014/0315242 A1 Oct. 23, 2014

Related U.S. Application Data

(63) Continuation of application No. 12/294,037, filed as application No. PCT/US2007/064893 on Mar. 26, 2007, now abandoned.

(60) Provisional application No. 60/785,877, filed on Mar. 24, 2006.

(51) Int. Cl.
| | |
|---|---|
| *G01N 33/04* | (2006.01) |
| *G01N 15/14* | (2006.01) |
| *B01L 3/00* | (2006.01) |
| *G01N 15/00* | (2006.01) |
| *G01N 1/28* | (2006.01) |

(52) U.S. Cl.
CPC ......... *G01N 33/04* (2013.01); *G01N 15/1463* (2013.01); *G01N 15/1484* (2013.01); *B01L 3/5027* (2013.01); *G01N 1/2813* (2013.01); *G01N 2015/008* (2013.01)

(58) Field of Classification Search
None
See application file for complete search history.

(56) References Cited

U.S. PATENT DOCUMENTS

| | | |
|---|---|---|
| 3,963,580 A | 6/1976 | Vedamthu |
| 4,190,020 A | 2/1980 | Tamas |
| 4,385,590 A | 5/1983 | Mortensen |
| 4,790,640 A | 12/1988 | Nason |
| 5,116,731 A | 5/1992 | Wilhelms |
| 5,168,044 A | 12/1992 | Joyce |
| 5,302,903 A | 4/1994 | De Jong |
| 5,306,719 A | 11/1994 | Levine |
| 5,434,082 A | 7/1995 | Yamamoto |
| 5,480,778 A | 1/1996 | Levine |
| 5,550,148 A | 8/1996 | West |
| 5,628,964 A | 5/1997 | Tassitano |
| 5,637,469 A | 6/1997 | Wilding |
| 5,660,993 A | 8/1997 | Cathey |
| 5,792,964 A | 8/1998 | Van den Berg |
| 5,807,684 A | 9/1998 | Simmons |
| 5,849,488 A | 12/1998 | Alatossava |
| 5,948,686 A | 9/1999 | Wardlaw |
| 6,004,821 A | 12/1999 | Levine |
| 6,038,030 A | 3/2000 | Van den Berg |
| 6,073,580 A | 6/2000 | Graupner |
| 6,127,184 A | 10/2000 | Wardlaw |
| 6,180,314 B1 | 1/2001 | Berndt |
| 6,197,538 B1 | 3/2001 | Van den Berg |
| 6,235,536 B1 | 5/2001 | Wardlaw |
| 6,287,771 B1 | 9/2001 | Imamura |
| 6,297,045 B1 | 10/2001 | Takahashi |
| 6,307,362 B1 | 10/2001 | Mangan |
| 6,330,350 B1 | 12/2001 | Ahn |
| 6,350,613 B1 | 2/2002 | Wardlaw et al. |
| 6,479,017 B2 | 11/2002 | Miefalk |
| 6,493,071 B2 | 12/2002 | Van den Berg |
| 6,658,143 B2 | 12/2003 | Hansen |
| 6,723,290 B1 * | 4/2004 | Wardlaw ............ B01L 3/502738 422/559 |
| 6,979,550 B1 * | 12/2005 | Rivas ................. G01N 33/5094 435/325 |
| 2002/0028158 A1 | 3/2002 | Wardlaw |
| 2002/0054831 A1 | 5/2002 | Van den Berg |
| 2002/0055178 A1 | 5/2002 | Wardlaw |
| 2002/0183600 A1 | 12/2002 | Tsenkova |
| 2002/0198441 A1 | 12/2002 | Tsenkova |
| 2004/0019300 A1 | 1/2004 | Leonard |
| 2006/0024756 A1 | 2/2006 | Tibbe et al. |

FOREIGN PATENT DOCUMENTS

| | | |
|---|---|---|
| EP | 1500935 A1 | 1/2005 |
| JP | 63019532 A | 1/1988 |
| JP | 63019532 A | 2/1988 |
| JP | 2001-248060 | 9/2001 |
| WO | WO 99/45365 | 9/1999 |

OTHER PUBLICATIONS

Feng et al., European Food Research and Technology, vol. 220, pp. 653-657 (electronically available Nov. 30, 2004).*
Feng et al., European Food Research and Technology, vol. 220, pp. 653-657; electronically available Nov. 30, 2004 (of record).*
European Search Report Corresponding to European Application No. 07759349.9; dated Feb. 17, 2014; 8 Pages.
Fluorescence-Assisted Transmigration Invasion and Motility Assay; date unknown but believed earlier than (Mar. 24, 2006).
Andrew Je Seely et al. Science review: Cell-membrane expression (connectivity) regulates neutrophil delivery, function and clearance; Critical Care 2003; Jan. 9, 2003; 7:291-307; doi:10.1186/cc1853.

(Continued)

*Primary Examiner* — Sharmila G Landau
*Assistant Examiner* — Paul D. Pyla
(74) *Attorney, Agent, or Firm* — Myers Bigel, P.A.

(57) ABSTRACT

The present invention relates to a device and method for the detection of mastitis or other disease from a body fluid of a mammal for example from cow's milk. The device and method relates to a wedge microfluidic chamber for using a minimal amount of fluid and being able to use the device to observe leukocytes in a mono-layer for the purpose of disease detection, cell counts or the like.

23 Claims, 3 Drawing Sheets

(56) References Cited

OTHER PUBLICATIONS

Dennis D. Taub et al. T Lymphocyte Recruitment by Interleukin-8(IL-8) IL-8-induced Degranulation of Neutrophils Releases Potent Chemoattractants fro Human T Lymphocytes Both In Vitro and In Vivo; J. Clin. Invest.; Apr. 1996; 1931-1941; vol. 97, No. 8, Baltimore, MD.
Fatima, Fluorescence-Assisted Transmigration Invasion and Motility Assay; Tecan.
Fernandez-Segura E. et al. Shape, F-actin, and surface morphology changes during chemotactic peptide-induced polarity in human neutrophils; PMID: 7604967 [PubMed—indexed for MEDLINE]; Anat Rec. Apr. 1995; 241(4):519-28; Departmento de Biologia Celular e Histologia, Facultad de Medicina, Universidad de Granada, Spain.
Gavin P. Sandilands et al. Cross-linking of neutrophil CD11b results in rapid cell surface expression of molecules, required for antigen presentation and T-cell activation; Immunology; vol. 114, Issue 3, p. 354, Mar. 2005; doi:10.1111/j.1365-2567.2004.02114.x.
Jasper et al. "Acridine Orange Staining for Diagnosis of Mycoplasma bovis infection in Cow Milk" Journal of Clinical Microbiology, vol. 20, No. 4, pp. 624-625 (1984).
Kokura S, Wolf RE, Yoshikawa T, Granger DN, AW TY; T-lymphocyte-derived tumor necrosis factor exacerbates anoxia-reoxygenation-induced neutrophil-endothelial cell adhesion: Circ Res.; Feb. 4, 2000; 86(2):205-13 PubMed.
Larry A. Harshyne et al. Dendritic Cells Acquire Antigens from Live Cells for Cross-Presentation to CTL; The Journal of Immunology, 2001, 166:3717-3723; The American Association of Immunologists: University of Pittsburgh, PA.
Leitner et al. "Milk Leucocyte Population Patterns in Bovine Udder Infection of Different Aetiology", J. Vet. Med. B, vol. 47, pp. 581-589 (2000).
Maurizio Provenzano, Simone Mocellin, Paola Bonginelli, Dirk Nagorsen, Seog-Woon Kwon and David Stroncek; Ex vivo screening for immunodominant viral epotopes by quantitative real time polymerase chain reaction (qRT-PCR); Journal of Translational Medicine, Dec. 15, 2003, 1:12; Journal of Translational Medicine.
Nicholas S. Potter and Clifford V. Harding; Neutrophils Process Exogenous Bacteria Via an Alternate Class I MHC Processing Pathway for Presentation of Peptides to T Lymphocytes: Department of Pathology, Case Western Reserve University, Cleveland, OH.
Oleg Chertov et al. Identification of Human Neutrophil-derived Cathepsin G and Azurocidin/CAP37 as Chemoattractants for Mononuclear Cells and Neutrophils; J. Exp. Med.; Aug. 29, 1997; 739-747; vol. 186, No. 5; Frederick, MD.
Perihan Nalbant, Louis Hodgson, Vadim Kraynov, Alexei Toutchkine, Klaus M. Hahn; Activation of Endogenous Cdc42 Visualized in Living Cells; Science: Sep. 10, 2004; 1615-1619; vol. 305, Science Magazine; Chapel Hill, NC.
Radsak M et al. Polymorphonuclear neutrophils as accessory cells for T-cell activation: major histocompatibility complex class II restricted antigen-dependent induction of T-cell proliferation; 1: Immunology Dec. 2000; 101(4):521-30; Institut for Immunologie and Medizinische Klinik der Universitat Heidelberg, Heidelberg, Germany.
Ron L. Bardell et al: "Microfluidic Disposables for Cellular and Chemical Detection-CFD Model Results and Fluidic Verification Experiments"; Proc. SPIE 4265, 1 (2001); doi: 10.1117/12.427961.
S.J. Molesworth-Kenyon et al. A novel role for neutrophils as a source of T cell-recruiting chemokines IP-10 and Mig during the DTH response to HSV-1 antigen; J Virol. Aug. 2002:76(16):8050-7; Department of Microbiology and Immunology, University of South Alabama; Mobile, AL.
S.J. Molesworth-Kenyon et al. A novel role for neutrophils as a source of T cell-recruiting chemokines IP-10 and Mig during the DTH response to HSV-1 antigen; Journal of Leukocyte Biology: 2005:77:552-559; Society for Leukocyte Biology; Department of Microbiology and Immunology, University of South Alabama; Moibile, AL.
Shigeo Yamashiro et al. Phenotypic and functional change of cytokine-activated neutrophils: inflammatory neutrophils are heterogenous and enhance adaptive immune responses: Journal of Leukocyte Biology; 2001; 69:698-704; Society for Leukocyte Biology, Laboratory of Molecular Immunoregulation, National Cancer Institute at Frederick, Frederick, MD.
Taras A. Lyubchenko, Georjeana A. Wurth, and Adam Zweifach; Role of Calcium Influx in Cytotoxic T Lymphocyte Lytic Granule Exocytosis During Target Cell Killing; Immunity; Nov. 2001; vol. 15, 1-20; Cell Press Denver, CO.
Terrence M. Tumpey et al; "Role for Macrophage Inflammatory Protein 2 (MIP-2) MIP-1α, and Interleukin-1α in the Delayed-Type Hypersensitivity Response to Viral Antigen"; J. Virol. Aug. 2002, 76(16): pp. 8050-8057.
Tilo Biedermann et al. Mast Cells Control Neutrophil Recruitment during T Cell-mediated Delayed-type Hypersensitivity Reactions through Tumor Necrosis Factor and Macrophage Inflammatory Protein 2; Journal of Experimental Medicine; Nov. 13, 2000; 1441-1452; vol. 192, No. 10; Rockefeller University Press.
Tumpey, TM et al. Role for macrophage inflammatory protein 2(MIP-2), MIP-1alpha, and interdeukin-1alpha in the delayed-type hypersensitivity response to viral antigen, PMID: 12134010 [PubMed—indexed for MEDLINE]; Southeast Poultry Research Laboratory, U.S. Department of Agriculture, Agriculture Research Service, South Atlantic Area, Athens, GA.
Tvinnereim, AR et al. Neutrophil involvement in cross-priming CD8+ T cell responses to bacterial antigens; PMID: 15265934 [PubMed—indexed for MEDLINE]; J. Immunol. Aug. 1, 2004; 173(3):1994-2002; Department of Microbiology, University of Iowa, Iowa City, IA.
K. Petrovski and E. Stefanov. Milk composition changes during mastitis. Milkproduction.com. (2006) 11 pages. Downloaded Jul. 1, 2016.

\* cited by examiner

MICROFLUIDIC CHAMBER ASSEMBLY FOR MASTITIS ASSAY

RELATED APPLICATIONS

This application is a continuation of U.S. patent application Ser. No. 12/294,037 filed on Sep. 22, 2008 which is a 35 U.S.C. § 371 national phase application of PCT International Application No. PCT/US2007/064893, filed Mar. 26, 2007, which claims priority claims priority of U.S. provisional patent application No. 60/785,877 filed on 24 Mar. 2006 incorporated herein by reference in its entirety.

BACKGROUND OF THE INVENTION

1. Field of the Invention

The present invention relates to microfluidic chamber for analyzing a subjects' body fluids, in particular milk, to determine if the subject has a bacterial infection such as bovine mastitis. Specifically, the invention relates to a chamber assembly which can be used to detect mastitis or other bacterial disease in bovine or other mammal species.

2. Description of the Related Art

Mastitis is the inflammation of the mammary gland caused by microorganisms that invade one or more quadrants of the bovine udder, multiply, and produce toxins that are harmful to the mammary gland. Economic loss to mastitis in the United States is estimated to be approximately $185/cow annually. The total annual US cost of mastitis is over $2 billion. This is approximately 10% of the total value of farm milk sales, and about two-thirds of this loss is due to reduced milk production in subclinically infected cows.

The average production loss per lactation for one infected udder quarter is about 1,600 pounds. Other losses are due to discarded abnormal milk and milk withheld from cows treated with antibiotic, costs of early replacement of affected cows, reduced sale value of culled cows, costs of drugs and veterinary services, and increased labor costs. Mastitis reduces milk yield and alters milk composition. The magnitude of these changes in individual cows varies with the severity and duration of the infection and the causative microorganisms. Mastitis is almost always caused by bacteria. These microorganisms produce toxins that can directly damage milk-producing tissue of the mammary gland, and the presence of bacteria initiates inflammation within the mammary tissue in an attempt to eliminate the invading microorganisms. The inflammation contributes to decreased milk production and is primarily responsible for the compositional changes observed in milk from infected quarters and cows. In general, compositional changes involve an increase in blood components present in milk and a decrease in normal milk constituents.

Clinical Mastitis includes visible signs of mastitis such as the "mild" signs, for example, flakes or clots in the milk, or slight swelling of an infected quarter. It also includes "severe" signs such as abnormal secretion; hot, swollen quarter or full udder; fever, rapid pulse, loss of appetite; dehydration and depression; and in some cases death may occur.

In Subclinical Mastitis there are no visible signs of the disease. Diagnosis of subclinical mastitis is characterized by the Somatic Cell Count (SCC) of the milk being elevated and the bacteriological culturing of milk will detect bacteria in the milk. Subclinical mastitis causes the greatest financial loss to dairy farmers through lowered milk production. For every clinical case of clinical mastitis, there will be 15 to 40 sub-clinical cases.

The SCC is the number of leukocytes or white blood cells per milliliter of milk. The SCC has become the standard procedure for diagnosing sub-clinical mastitis and is also used worldwide as the index of milk quality. The SCC enumerates the many cells that populate the milk-producing gland as part of the immune defense system, and then cross the blood/milk barrier, as well as the few epithelial cells that line the udder, and also get into the milk. In response to infection, the animals' immune systems produce an "inflammatory response" in the gland and more of the infection-fighting white cells (mostly neutrophils) find their way into the milk. The SCC is reported as "the sum", the total of those cells. Normal milk will have less than 200,000 cells per milliliter. An elevated SCC (200,000 and over) is an indication of inflammation in the udder. The SCC is the current measure for commercial acceptability for milk in many countries, for example milk with an SCC over 400,000 can not be sold in Europe. Other countries limits include Canada, 500,000 and the United States 750,000 (600,000 in California). Currently there is no SCC associated with Clinical Mastitis.

The SCC is also used in bulk tank management, in determining the suitability for shipment, in making culling decisions and in the payment of quality bonuses. In summary, the SCC, a single number, is everywhere in the dairy industry and it is used in almost every area of milk production. The SCC led to increases in productivity, losses due to clinical-stage mastitis being stabilized, and the generally accepted notion that the milk supply is safe.

The SCC is not a number representing a single type of leukocyte, rather it is a mixture of multiple types of leukocytes, each with its own significance. In milk from a healthy animal, the predominant cell types are lymphocytes, followed by much lesser numbers of neutrophils and macrophages. The percentages of each kind of cell rise and fall as part of the immune response to infection. Those percentages, "the differential milk leukocyte count", represent the unique immune status of an individual quarter udder, at a specific point in time. The literature has suggested that a better understanding of the dynamics of mastitis could be accomplished by specifically measuring the rise and fall in the types of leukocytes involved in the disease process and recovery. The literature has also specifically identified the normal differential pattern of uninfected cows at various stages of lactation, it has suggested algorithms to identify the various stages of infection by looking at changes in those patterns and it has suggested linkages of specific abnormal patterns to specific pathogens. In 2005, Hamman used the differential pattern to show quarters were inter-dependent. Essentially, the literature suggests that the breakdown of the SCC into its component parts, the "milk somatic cell differential", should be a better, more accurate and specific indicator of udder health, and thus a better tool for the management of mastitis. However, in spite of the evolving evidence, the SCC continues to be reported as a total SCC, and the differential information remains a research tool. This is primarily been driven by the cost differential between the SCC and computations for a differential.

At least two procedures are currently used in the determination of the bovine SCC with a leukocyte differential. One method is using flow-cytometry, an expensive, sophisticated tool only found in top research laboratories. This method is not even remotely practical for the farmer. Its only alternative, the "manual milk differential smear" (MMDS), is a difficult and time consuming procedure, subject to great variability, even when performed by highly trained laboratory technologists. It is impractical for field research or the barn environment as well.

In order to perform an MMDS, milk is centrifuged at 2500 g for 10 min at 4 degrees Celsius, the fat layer and supernatant are removed, leaving 500 µl or less of milk with a pellet. The pellet is re-suspended via vortexing and pipetting. Microscope slides are coated with Trypticase Soy Broth, air-dried and 10 µl of milk is placed on the slide for a 30-degree angle smear to be made. The slide is allowed to air dry and is then stained with Wright Giemsa Stain. The slide is placed in the stain for 15 seconds, then water for 30 seconds, then a 15 second dip in clean water and finally it is allowed to air dry. Slides are examined on a transmitted light microscope with a 100× oil immersion lens.

In U.S. Pat. No. 6,350,613 to Wardlaw, there is described a device and method for determination of white blood cell differential counts. The slide described in FIG. 1 is a wedge type slide comprising a microscope slide base, a slip cover wedge top and a rectilinear shim at the top part of the wedge. This design is described primarily for blood but is taught to be useful for any leukocyte containing liquid for example milk. The device suffers from some difficulties in use. First since the cover slip end opposite the shim is not fixed the end can leak, shift or get caught on other objects during use. Second since the design involves a shim the entire length of the cover slip there is no easy way to place the liquid in the chamber.

FIG. 2 in the Wardlaw patent describes the appropriate angle for creating a wedge sampling configuration for us in differential testing. Accordingly, it would be very useful to have a different wedge chamber design that overcomes the limitations of the prior art teachings.

BRIEF SUMMARY OF THE INVENTION

It is an object of the invention to provide both an assay and a novel microfluidic slide assembly using the wedge design that can be used to test leukocyte containing body fluids such as bovine milk for a leukocyte differential test. It is an object to make the test and slide useful for the farmer in the field and easy enough for a farmer to do or at least prepare. The test is relatively quick, easy to do, accurate, wherein the slide is disposable. The farmer can do the test in the field and use very small volumes of milk. The above objectives and more are achieved by the present invention and are distinct novel advantages as can be further seen from the disclosure herein.

One embodiment of the device is microfluidic chamber assembly for use in performing leukocyte differential assay on a leukocyte containing fluid sample from a subject in a wedge sampling configuration chamber comprising:
  a) an wedge base;
  b) a wedge top forming the angle part of the wedge;
  c) a wedge forming device which secures a first edge of the top to the base forms the bottom edge of the wedge chamber, elevates and secures the opposite second edge of the top from the base to form a wedge chamber and provides for a liquid entry well for liquid addition to the chamber;
  wherein at least one of the base or top is optically transparent.

The assay itself comprises in one embodiment, method for performing a leukocyte differential assay comprising:
  a) adding a leukocyte containing liquid to the chamber of a slide assembly of claim 1;
  b) enumerating and calculating the leukocytes in the liquid containing chamber into sub-populations; and
  c) deriving a differential count of the leukocyte sub-populations.

Other embodiments and variations will be obvious from the disclosure, teachings and examples herein.

DETAILED DESCRIPTION OF THE INVENTION

Figure 1:
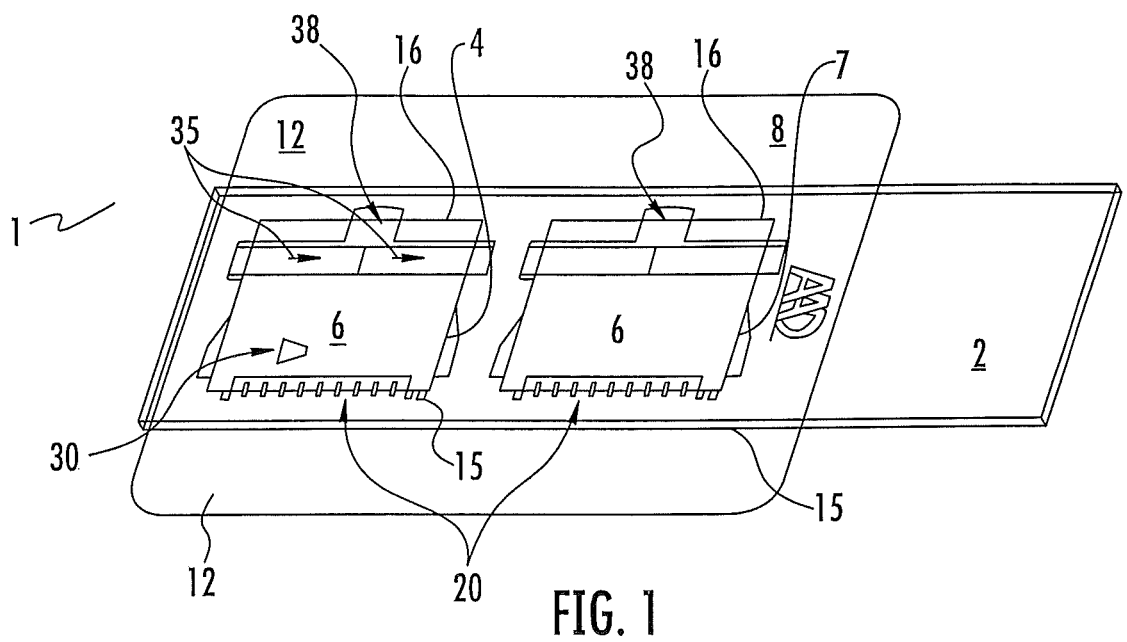
FIG. 1 shows an embodiment of the invention with a dual chamber mounted on a base.

The present invention relates to a novel microfluidic wedge chamber and a leukocyte differential assay (LDA) for determination if a subject has mastitis in a given sample of milk. The general description of both the device and method are stated in the Brief Summary above. This detailed description defines the meaning of the terms used herein and specifically describes embodiments in order for those skilled in the art to practice the invention. The assay is done exposing leukocyte containing body fluid such as bovine milk, whole blood or other leukocyte containing body fluid such as lymph fluid, spinal fluid or the like, to a predetermined cell count in the device of the invention. The test is compared for difference in leukocyte types and those differences determine if the subject has mastitis i.e. if the leukocyte SCC is 200,000 or greater and what the breakdown of different leukocytes within that population is. A distinct advantage of the assay of the invention is that it is not only qualitative in nature, it is quantitative in nature and therefore leukocyte such measurements are more telling of the exact condition of the subject bovine patient.

By "subject" is meant herein to be any animal especially bovine and especially bovine milk containing leukocytes. In addition other birds, mammals and especially humans, that have body fluids containing leukocytes. The primary assay of the invention is use of the chamber to test for bovine mastitis but the chamber could simply be used to make a leukocyte determination for other bodily fluids for example as taught in the Wardlaw patent described above.

By "leukocyte" is meant any of the sub categories of leukocytes that are known to exist in milk or blood or other bodily fluid. These sub-categories can be identified and quantified with the device and assay of the invention especially for the detection of mastitis or other leukocyte based disease states.

By "wedge base" is meant a substrate sufficient for performing a leukocyte differential determination. In one embodiment the base would be a microscope slide made of glass or plastic and optionally optically transparent. It is clear however that where the determination is made with observation and lighting from the top of the assembly, that the base could be a non-transparent material such as paper or opaque plastic.

By "Wedge top" is meant a substrate which forms the angle top wall of a chamber such as described in Wardlaw. In one embodiment that top portion is a slide cover slip of glass or plastic which is positioned to form a wedge chamber for making cell count differential determinations. It is an embodiment that the wedge top be optically transparent but where a reading is taken from the bottom the top may be opaque and be of a material other than plastic or glass including paper cardboard, metal or the like.

By "wedge forming device" is meant a device which by its design accomplishes 4 important functions. First, it secures an edge of the wedge top to the base. Second, it secures the opposite edge of the top in an elevated configuration such that the wedge shaped chamber is formed sufficient for cell differential determination. One skilled in the art as taught above would easily be able to determine the proper angles for such chamber. Third, it secures the opposite side in such a manner that it may not move during normal use and fourthly, it provides a cut-out well so that liquid may be added to the top portion of the wedge instead of from the side as in previous prior art wedge chambers. This is accomplished by use of an adhesive backed film in one embodiment. The adhesive film is cut out in such a manner that a flap for adhesion of one side of the top is formed. The film also has a cut out portion allowing for an unobstructed view of the top and base. Further it provides a means for securing the top edge of the top and it also provides a cut out portion for a liquid addition well. The wedge configuration of the chamber is then formed by one edge of the top resting against the base and the other opposite edge of the top resting on the film, the thickness of the film determines the shape and volume of the chamber. In general, where the base is a microscope slide and the top a slide slip cover the film would be chosen to be about 0.04 to 0.06 mm more or less in thickness. In one embodiment, the film is 0.05 mm in thickness. As can be seen in the figures, the adhesive allows the film to be attached to the base and the top simultaneously because of the adhesive backing and the unique cut-out design. The film is in an embodiment a polymer which gives it both flexibility and ease of putting an adhesive backing thereon. The adhesive should be such that it adheres to both the top and base and one skilled in the art would be able to make optimum choices depending on the materials chosen for the top and base.

In the assay, by "enumerating and calculating" is meant that the liquid in the chamber is observed by methods taught for differentiation (see Example) and thus the chamber allows for differentiation of the leukocyte sub-population. By deriving a differential count" is meant that once the sub populations of the ample are determined that a count of each of the sub populations is made such that the sub population of the total SCC count can be determined.

"Leukocyte observation colorants" are compounds known to differentially color morphological factors, in a leukocyte and cause various colorations (spectral factors) at various wavelengths based on the leukocytes reaction or lack of reaction to the antigen. Examples of such colorants include but are not limited to: Astrozone Orange, Also known as Basic Orange 21 which is 3-trimethyl-2(2-(2-methyl-1H-indol-3-yl)-vinyl)-3H-indolium chloride. Other possible colorants include Acridine Orange, Ethidium Bromide, Griefswalder's Blue, Blue Borrel, Rhodanile Blue, Toluidine Blue, Night Blue, Prune Pure, Hofmann's Violet, Basic Red 13, Basic Violet 16, Carbocyanine K-5, and mixtures of above. Many of the colorants are cytotoxic. When selecting a cytotoxic colorant it is preferable to allow it to be in contact with cells the minimum time. In the embodiment of the invention where the observation and reaction chambers are separate the minimum time in contact is achieved. Where the predetermined time is short enough or the colorant is not cytotoxic the embodiment where the reaction and observation microchambers of each test are the same microchamber can be used.

The "chamber" is a chamber for which leukocytes measurement factors can easily be observed by optical scan. The is designed to spread out the fluid sample in such a manner to make a field by field, YYZ scan possible. See, for example, U.S. Pat. No. 6,350,613 which describes such chamber and optical scan thereby.

In one embodiment of the invention the device is made in a disposable format. This device would be made of plastic, glass or other inexpensive disposable material. The device of the invention containing the subject sample can be discarded in an appropriate manner and the tester need never come in contact with the contents. The disposable microfluidic device can be constructed credit card size more or less similar to other microfluidic assays such that it fits in a reader portion of an image analyzer that can read the colorimetric data from the tests by either moving the test device around or moving a reader in the analyzer or both to take readings of the type in the above referenced patents and also described herein. A microscopic slide size will also be useful.

Turning now to the figures FIG. 1 is an embodiment of the invention wherein two wedge chambers are shown suitable for two assays. The microfluidic assembly 1 consists of the wedge base 2, which in this case is a microscopic glass slide. Other materials including plastics can be used for the wedge base 2 Wedge base 2 is shown as a rectangle but one skilled in the art could chose what ever shape necessary or desired to accommodate the assay or assay machine. In this view the Wedge base 2 is a microscope slide. A slide is a good embodiment since slides are readily available in both glass and plastic and normally come optically transparent. In the embodiment in FIG. 1 there are actually two Microfluidic chambers since based on the size of the chambers it is easy to place multiple chambers on the base 2. However, it is clear that one skilled in the art could place one or depending on their size more than two on the base 2. The wedge top 6 in this embodiment is a microscope slide slip cover and has a first edge 15 and an opposite second edge 16. Thin glass is used in this embodiment but plastic and other thicknesses as desired could be substituted as well.

The wedge forming device 8 is a piece of cut out plastic sheeting with an adhesive backing facing the wedge base 2. The wedge forming device 8 is placed against the base 2 so that it adheres. There are extra portions 12 that extend beyond the base 2. These extra portions can be folded underneath the base 2 to form a stronger bond to the base 2. The functioning of the wedge forming device 8 will be clear now upon looking at this embodiment. The scored hold down flap 20, adheres to the top 6 and holds the first edge 15 securely against the base 2 forming the bottom point of a chamber 30. The second opposite edge 16 rests on the upper surface of the wedge forming device 8 such that it forms the high point under the top 6 of chamber 30. The top 6 is held down in place on the upper surface of wedge forming device 8 by two arms 35 which fold over the top and adhere to the tops upper surface. A last feature in the wedge forming device 8 is a cut out for a liquid addition well 38. to perform the assay a liquid for example bovine milk is placed in well 38 and spreads out evenly in chamber 30. The design of the chamber is such that at the first end of the top the area under the top is such that a single layer of cells is created within chamber 30.

Example

Assay for Milk Somatic Cell Differential Counts

In one embodiment of the assay, 80 µl of milk is mixed with 20 µl of a meta-chromatic stain, gently mixed, and a small drop of the mixture is placed in the deposition well of a slide of the invention. The wedge of the slide chamber fills automatically by capillary action, the cells in the milk are distributed evenly at optimum locations, and are ready for observation in seconds. A pre-concentration step may be required for very low SCC samples. The wedge can be aptly described as a "self preparing wet smear."

Once the wedge slide has self-prepared, it is ready for immediate analysis by one of three methods:
(a) Visual identification by direct observation of the various live, intact, fluorescing cells, using a simple fluorescence microscope (for use by the experienced milk researcher); (b) Visual identification of the various cells using computer-enhanced digital camera images in a computer screen (for the use of a laboratory cytology technician) or (c) Automatic counts of the cells by a simple imaging instrument requiring minimum operator training (for use by non-laboratory personnel in the milking barn).

Principle of the Image Computer Enhancement

Figure 2:
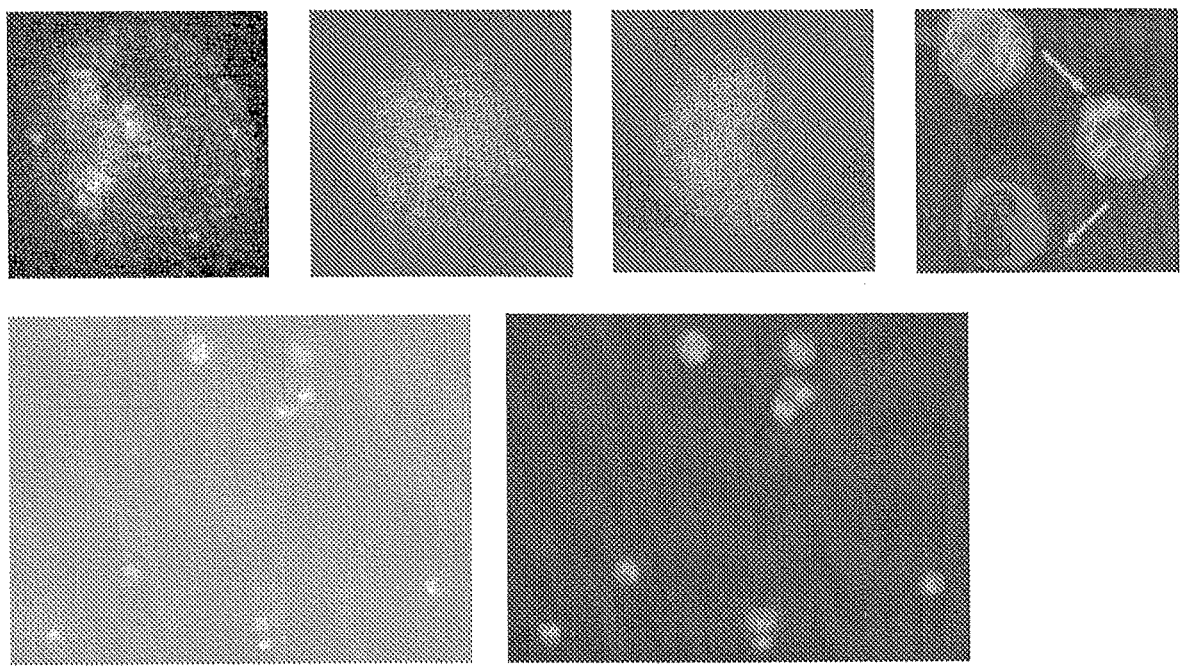
FIG. 2 displays enhanced images produced by an embodiment of the invention.

Multiple fluorescence images at different wavelengths are captured and the resulting "enhanced image" is displayed for easy identification by the lab technician as shown in FIG. 2.

Principle of the Simple Automatic Counter

In the on-site simple reader version, the enhanced imaged is analyzed using mathematical features captured by software derived from face-recognition/machine-vision research, and a report of the percent of each of the three inflammatory cells is presented, as well as total SCC.

Variety of Differential Patterns

The variance of result is illustrated by a few examples of the variety of patterns present in cows. The graphs below suggest that not all cows with the same SCC may be assumed to have the same health status, and that the ratio of differential cells may indeed have clinical relevance.

Figure 3:
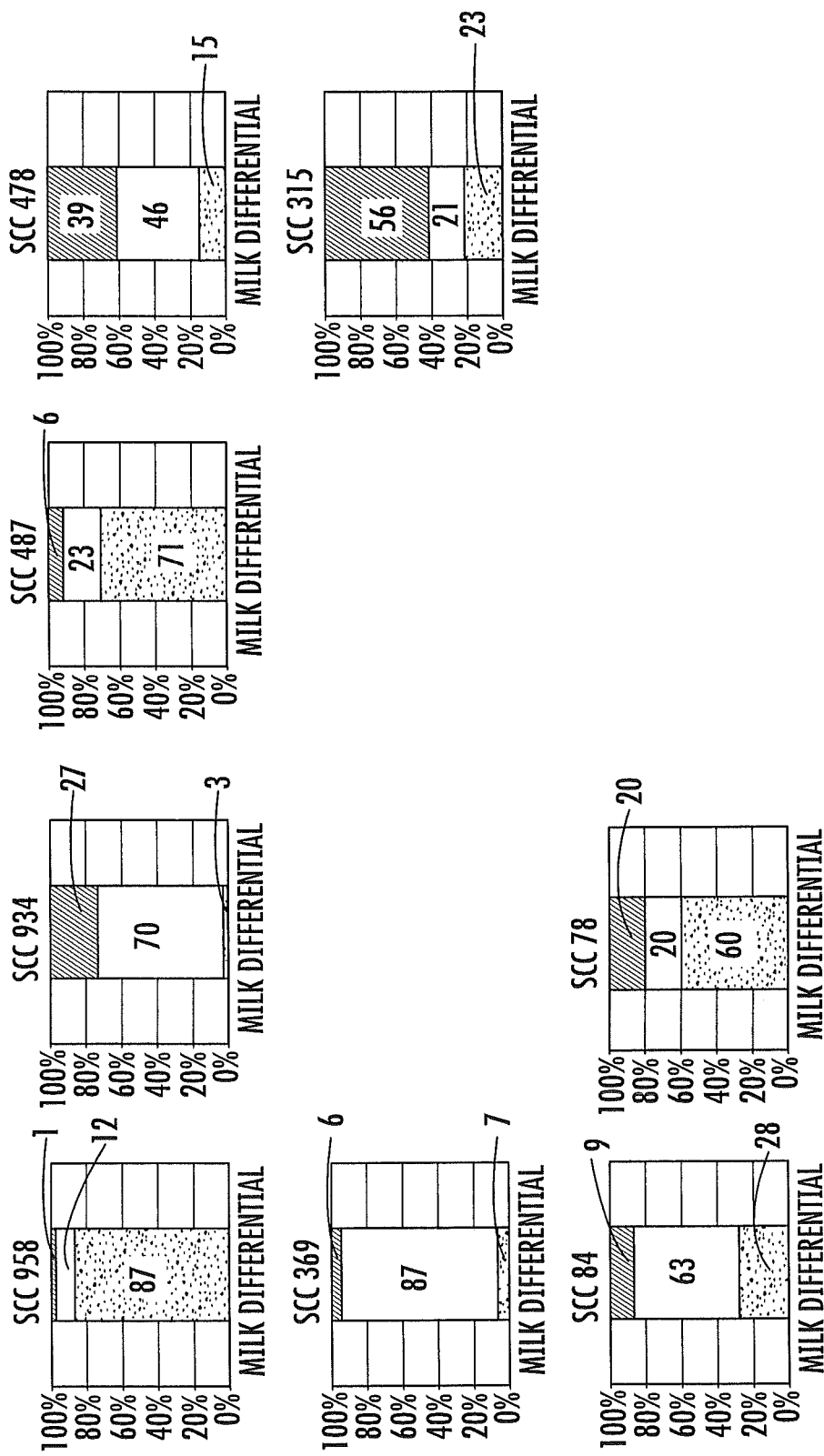
FIG. 3 displays graphs of the resultant cell count produced by an embodiment of the present invention.

The dark areas are % PMN, the light areas are % lymphocytes and the cross hatched areas are % macrophages. SCC is .times.1000 cells/ml for all examples. See FIG. 3.

Visual Identification of Computer-Enhanced Images Vs. Manual Differential Smear

Composite samples (n=85) from Holstein dairy cows were collected from North Carolina farms. For each milk sample, a smear.sup.4 was prepared from an aliquot, using the Wright-Giemsa stain method, and a "one hundred cell differential" was performed using light microscopy. The test method was prepared from a second aliquot and enhanced images were collected. A certified technologist identified one hundred cells from those images. Comparison of results is shown.

| | Correlation of Visual ID vs. One Hundred Cell Smear |
|---|---|
| Neutrophils (PMN) | $R^2 = 0.763$ |
| Lymphocytes | $R^2 = 0.786$ |
| Macrophages/Epithelial | $R^2 = 0.713$ |

Automatic Counts of the Inflammatory Cells by the Simple Imaging Instrument

Quarter samples (n=122) from Holstein dairy cows were collected from North Carolina farms. For each milk sample, a smear was prepared from an aliquot, using the Wright-Giemsa stain method, and a "two hundred cell differential" was performed using light microscopy. The test method was prepared from a second aliquot and enhanced images were collected. The instrument software identified two hundred cells from those images. Comparison of results is shown.

| | Correlation of Instrumented ID vs. Two Hundred Cell Smear |
|---|---|
| Neutrophils (PMN) | $R^2 = 0.794$ |
| Lymphocytes | $R^2 = 0.863$ |
| Macrophages/Epithelial | $R^2 = 0.724$ |

The results obtained with this assay match the statistically expected performance when evaluating manual/visual differential leukocyte counting methods, and we therefore conclude there is reasonably good agreement between it and the more difficult milk differential smear. This new method is a tool to help in the routine management of mastitis. Possible applications of the newly available information include: (a) Stage the disease, (b) an indicator for determining whether to culture, (c) an indicator as far as which fully symptomatic clinical cows are likely to get better, (d) an early warning of mastitis in peri-partum or early lactation, (e) differentiate between a high SCC due to lactation and a high SCC due to intra-mammary infection, (f) confirm quarters with mastitis after positive "in-line" conductivity measurement.

REFERENCES

1. Anderson K L, et al. PMN leukocyte function in clinical bovine patients and in cows with or without *Staphylococcus aureus* mastitis. Vet Res Com1992; 16(2):107-115
2. Doboo I R, et al. Use of total and differential somatic cell counts from composite milk samples to detect mastitis in individual cows. Can J Comp Med. 1981; 45 (1): 8-14
3. Dosogne H, et al. Differential leukocyte method for bovine low somatic cell count milk. J Dairy Sci. 2003; (3): 828-34
4. Dulin A M, et al. Cytospin centrifuge in differential counts of milk somatic cells. J Dairy Sci. 1982; 65: 1247-1251
5. Emanuelson U, et al. Potential of differential somatic cell counts as indicators of mastitis in quarter milk samples from dairy cows. Acta Vet Scand 1989; (4): 475-81
6. Hamman J, et al. Differential cell count and interdependence of udder quarters, Proceedings IDF Congress on Mastitis and Milk Quality, June 2005
7. Kelly M et al. Correlation between bovine somatic cell counts and PMN Leukocyte levels for samples of bulk milk and milk from individual cows, J Dairy Sci 2000; 83:77:619-627
8. Kitchen B J. Review of the progress of dairy science bovine mastitis, milk compositional changes and related diagnostic tests. J Dairy Sci 1981; 48:167-188
9. Koepke J A, et al. A critical evaluation of the manual/visual differential leukocyte counting method. Blood Cells 1985: 11:173-186
10. Leitner G, et al. Milk leukocyte population patterns in bovine udder infection of different aetiology. Journal Vet Med B 2000; 47, 581-589
11. Miller R H, et al. Flow cytometric analysis of neutrophils in cow's milk. Am Vet Res 1993; 54:1975-1979
12. Paape, M J, et al. Historical perspective on the evolution of the milk somatic cell count. Flem. Vet. J. Suppl., 66:93
13. Pillai, S R et al. Application of differential inflammatory cell count as a tool to monitor udder health. J Dairy Sci 2001; 84:1413-1420
14. Redelman D. A mastitis monitoring program using the differential inflammatory cell count (DICC) Pages 219-220, Proc 34.sup.th Annual Meeting, NMC, 1997

15. Rivas, A L, et al. Longitudinal evaluation of bovine mammary gland health status by somatic cell counting, flow cytometry and cytology. 2001; J Vet Diagn Invest 13:399-407
16. Rumke C L. Expected Variability in Differential Leukocyte Counting. In John A. Koepke (Ed.), Differential Leukocyte Counting (pp. 39-45). Aspen: CAP 1977
17. Schroder A C, et al. The influence of technical factors on differential cell count in milk. J Dairy Research 2005; 72: 153-158

The previous examples are not intended to be limiting. One skilled in the art would be able to form other cut-outs, make various material choices and be able to apply the novel design to other assays involving cell differential and the like. The disclosure and the claims are therefore not intended to be limiting.

That which is claimed is:

1. A method for performing a leukocyte differential assay on a milk sample, said method comprising:
   (a) adding a milk sample comprising live cells to a microfluidic chamber assembly comprising:
      (i) a wedge base;
      (ii) a wedge top having a first top edge and an opposite second edge positioned on the base such that the second top edge is in an elevated configuration; and
      (iii) a cut out well positioned to add the milk sample comprising live cells to the wedge; wherein the wedge top is secured to the base in the elevated position, wherein at least one of the top or base is optically transparent and wherein there is a leukocyte observation colorant positioned within the chamber, wherein:
      when the sample is received in the well, the sample flows through a void between the top and the base and into the chamber via capillary action; and
      the milk sample forms a mono-layer of cells in the chamber;
   (b) observing in an automatic reader an image morphology of live cell leukocytes in the chamber;
   (c) enumerating and calculating the leukocytes in the milk containing chamber into sub-populations based on the observation of the image morphology of live cell leukocytes in the chamber; and
   (d) deriving a differential count of the leukocyte sub-populations;
   wherein the assay is performed in said automatic reader, wherein a differential is performed by the reader on a milk sample placed in the microfluidic chamber and the chamber placed in the reader.
2. The method according to claim 1, further comprising determining the presence of mastitis in the milk responsive to the differential count of leukocyte sub-populations.
3. The method according to claim 1, wherein the step of enumerating and calculating the leukocytes in the milk sample is performed on fluorescing live cells in a fluid milk sample and the leukocyte observation colorant is a fluorescing colorant.
4. The method according to claim 3, wherein the leukocyte observation colorant is a mixture of fluorescing colorants.
5. The method according to claim 1, wherein the microfluidic chamber assembly further comprises a wedge forming device that secures the first top edge and the opposite second edge to the wedge base so that the second top edge is in an elevated configuration.
6. The method according to claim 5, wherein the wedge forming device comprises a sheet having an adhesive and configured to mount the top to the base.
7. The method according to claim 6, wherein said top is optically transparent.
8. The method according to claim 6, wherein the wedge forming device further comprises a liquid entry well for liquid addition to the chamber.
9. The method according to claim 1, wherein each base comprises one or more chambers thereon.
10. The method according to claim 1, wherein observing an image morphology of live cell leukocytes comprises generating a computer-enhanced image using recognition software.
11. The method according to claim 1, wherein adding a milk sample comprising live cells to a microfluidic chamber assembly comprises a self-preparing wet smear.
12. The method according to claim 1, wherein enumerating and calculating the leukocytes in the milk comprises determining a health status based on a percentage of lymphocytes, neutrophils and macrophages in the sample.
13. The method according to claim 12, wherein the health status is a stage of disease.
14. The method according to claim 13, wherein the stage of disease comprises a stage of mastitis.
15. The method according to claim 13, wherein the stage of disease comprises mastitis in peripartum and/or early lactation.
16. A method for the automated imaging of live cell leukocyte morphology in a milk sample, said method comprising:
   (a) adding a milk sample comprising live cells to a microfluidic chamber assembly comprising:
      (i) a wedge base;
      (ii) a wedge top having a first top edge and an opposite second edge positioned on the base such that the second top edge is in an elevated configuration; and
      (iii) a cut out well positioned to add the milk sample comprising live cells to the wedge; wherein the wedge top is secured to the base in the elevated position, wherein at least one of the top or base is optically transparent and wherein there is a leukocyte observation colorant positioned within the chamber, and wherein:
      when the sample is received in the well, the sample flows through a void between the top and the base and into the chamber via capillary action; and
      the milk sample forms a mono-layer of cells in the chamber; and then
   (b) observing in an automatic reader an image morphology of live cell leukocytes in the chamber; and
   (c) identifying leukocyte subpopulations based on the image morphology of live cell leukocytes in the chamber.
17. The method according to claim 16, wherein the leukocyte observation colorant is a mixture of fluorescing colorants.
18. The method according to claim 16, wherein observing an image morphology of live cell leukocytes comprises generating a computer-enhanced image using recognition software.
19. The method according to claim 16, wherein said leukocytes comprise lymphocytes, neutrophils and macrophages.
20. The method according to claim 1, wherein the cut out well is positioned to add the milk sample comprising live cells to a top portion of the wedge at the second top edge.

21. The method according to claim 16, wherein the cut out well is positioned to add the milk sample comprising live cells to a top portion of the wedge at the second top edge.

22. The method according to claim 1, wherein observing an image morphology of live cell leukocytes comprises imaging the live cell leukocytes with a simple fluorescence microscope.

23. The method according to claim 16, wherein observing an image morphology of live cell leukocytes comprises imaging the live cell leukocytes with a simple fluorescence microscope.

* * * * *